US012622686B2

(12) United States Patent
Locke

(10) Patent No.: US 12,622,686 B2
(45) Date of Patent: May 12, 2026

(54) SURGICAL VESSEL CLOSING PRESSURE DEVICE

(71) Applicant: Catheter Precision, Inc., Fort Mill, SC (US)

(72) Inventor: Auston Locke, San Clemente, CA (US)

(73) Assignee: Catheter Precision, Inc., Fort Mill, SC (US)

( * ) Notice: Subject to any disclaimer, the term of this patent is extended or adjusted under 35 U.S.C. 154(b) by 847 days.

(21) Appl. No.: 17/867,205

(22) Filed: Jul. 18, 2022

(65) Prior Publication Data

US 2023/0270423 A1 Aug. 31, 2023

Related U.S. Application Data

(60) Provisional application No. 63/314,030, filed on Feb. 25, 2022.

(51) Int. Cl.
*A61B 17/00* (2006.01)
*A61B 17/04* (2006.01)
(Continued)

(52) U.S. Cl.
CPC ..................... *A61B 17/0057* (2013.01); *A61B 2017/00659* (2013.01); *A61B 2017/00663* (2013.01); *A61B 2017/00676* (2013.01); *A61B 17/0483* (2013.01); *A61B 2017/0496* (2013.01); *A61B 17/132* (2013.01); *A61B 2090/036* (2016.02); *A61B 2560/0285* (2013.01)

(58) Field of Classification Search
CPC ........ A61B 17/0487; A61B 2017/0496; A61B 17/0483; A61B 17/0469; A61B 17/0057; A61B 2017/0488; A61B 2017/0414; A61B 17/0401
See application file for complete search history.

(56) References Cited

U.S. PATENT DOCUMENTS 5,057,118 A * 10/1991 Picha ................... A61B 17/122
606/157
5,304,184 A * 4/1994 Hathaway .......... A61B 17/0469
606/144
(Continued)

FOREIGN PATENT DOCUMENTS

CN 104586455 A 5/2015
EP 2214564 B1 2/2017
WO 2009/114811 A2 9/2009

OTHER PUBLICATIONS

Copending U.S. Appl. No. 18/079,457, Inventors: Auston Locke, et al, Title: Surgical Vessel Closing Pressure Device, filed Jun. 11, 2021, 62 pages.
(Continued)

*Primary Examiner* — Darwin P Erezo
*Assistant Examiner* — Mitchell Brian Hoag
(74) *Attorney, Agent, or Firm* — The Marbury Law Group, PLLC

(57) ABSTRACT
Various embodiments include a vessel clamping pressure device that is configured to receive suture threads extending from the closure of a vascular vessel of a patient, and maintaining tension on suture threads between the patient and the vessel clamping pressure device to apply pressure to the patient so as to apply a clamping pressure to the vascular vessel to facilitate clotting.

11 Claims, 12 Drawing Sheets

(51) Int. Cl.
    *A61B 17/132*        (2006.01)
    *A61B 90/00*        (2016.01)

(56)            References Cited

U.S. PATENT DOCUMENTS

| | | | |
|---|---|---|---|
| 5,425,705 A | | 6/1995 | Evard et al. |
| 5,746,755 A | * | 5/1998 | Wood ................... A61L 24/106 |
| | | | 606/213 |
| 7,867,253 B2 | | 1/2011 | McMichael et al. |
| 8,267,942 B2 | * | 9/2012 | Szabo ................ A61B 17/0057 |
| | | | 606/232 |
| 8,721,664 B2 | | 5/2014 | Ruff et al. |
| 8,916,077 B1 | | 12/2014 | Goraltchouk et al. |
| 9,636,106 B2 | | 5/2017 | Meier et al. |
| 11,382,609 B2 | * | 7/2022 | Agnihotri .......... A61B 17/0401 |
| 11,672,524 B2 | | 6/2023 | Sampson et al. |
| D1,050,358 S | | 11/2024 | Sofy et al. |
| 2003/0229361 A1 | | 12/2003 | Jackson |
| 2004/0138706 A1 | | 7/2004 | Abrams et al. |
| 2005/0096699 A1 | | 5/2005 | Wixey et al. |
| 2006/0095073 A1 | | 5/2006 | Beto et al. |
| 2006/0241579 A1 | * | 10/2006 | Kawaura ............ A61B 17/0057 |
| | | | 606/42 |
| 2007/0032799 A1 | | 2/2007 | Pantages et al. |
| 2007/0151116 A1 | | 7/2007 | Malandain |
| 2007/0179528 A1 | | 8/2007 | Soltz et al. |
| 2007/0219467 A1 | * | 9/2007 | Clark .............. A61M 25/09041 |
| | | | 600/585 |
| 2009/0069847 A1 | * | 3/2009 | Hashiba ............. A61B 17/0487 |
| | | | 606/232 |
| 2010/0087837 A1 | | 4/2010 | Jaramillo et al. |
| 2010/0217202 A1 | | 8/2010 | Clark |
| 2010/0292733 A1 | * | 11/2010 | Hendricksen ...... A61B 17/0401 |
| | | | 606/232 |
| 2010/0305609 A1 | * | 12/2010 | Cartledge .......... A61B 17/0487 |
| | | | 606/232 |
| 2011/0125185 A1 | | 5/2011 | Stopek et al. |
| 2011/0152889 A1 | * | 6/2011 | Ashland ............. A61B 17/0487 |
| | | | 606/144 |
| 2011/0196205 A1 | | 8/2011 | Hathaway et al. |
| 2011/0196417 A1 | | 8/2011 | Clark |
| 2011/0208203 A1 | | 8/2011 | Melsheimer |
| 2012/0296347 A1 | * | 11/2012 | Roorda .............. A61B 17/0482 |
| | | | 606/145 |
| 2016/0022459 A1 | | 1/2016 | Price et al. |
| 2017/0014124 A1 | | 1/2017 | Lear |
| 2018/0008280 A1 | | 1/2018 | Clark |
| 2018/0055497 A1 | | 3/2018 | Pandya et al. |
| 2018/0368826 A1 | * | 12/2018 | Bonutti .............. A61B 17/0401 |
| 2019/0247043 A1 | * | 8/2019 | Gittard .............. A61B 17/0487 |
| 2019/0298335 A1 | | 10/2019 | Demir |
| 2019/0343633 A1 | * | 11/2019 | Garvin .............. A61B 17/0401 |
| 2020/0289109 A1 | * | 9/2020 | Chavan ................ A61B 17/683 |
| 2021/0298741 A1 | | 9/2021 | Eaves et al. |
| 2024/0156586 A1 | * | 5/2024 | Gabel ................ A61B 17/8869 |
| 2024/0320136 A1 | | 9/2024 | Zhou et al. |

OTHER PUBLICATIONS

Copending U.S. Appl. No. 18/124,386, Inventors: Auston Locke, et al., Title: Surgical Vessel Closing Pressure Device, filed Mar. 21, 2023, 68 pages.
Copending U.S. Appl. No. 18/138,200, Inventors: Auston Locke, et al., Title: Surgical Vessel Closing Pressure Device with Pressure Sensitive Film, filed Mar. 21, 2023, 71 pages.
Copending U.S. Appl. No. 29/862,677, Inventor: David Jenkins, Title: Vessel Closing Device, filed Dec. 12, 2022, 27 pages.
Inari Medical, FlowStatis™, "A simple solution for rapid hemostatis following percutaneous venous interventions", 11 pages.
International Search Report and Written Opinion received from the Korean Intellectual Patent Office in related International Application No. PCT/US2022/037606 dated Nov. 23, 2022.
Korean Intellectual Property Office, "International Preliminary Report on Patentability", issued in related International Application No. PCT/US2022/037606, mailed on Sep. 6, 2024 (7 pages).
JP Patent and Trademark Office; JP Application No. 2024-550307; Office Action mailed Aug. 6, 2025; 14 pages.
JP Patent and Trademark Office; JP Application No. 2024550307; Office Action mailed Jan. 26, 2026; 16 pages.

* cited by examiner

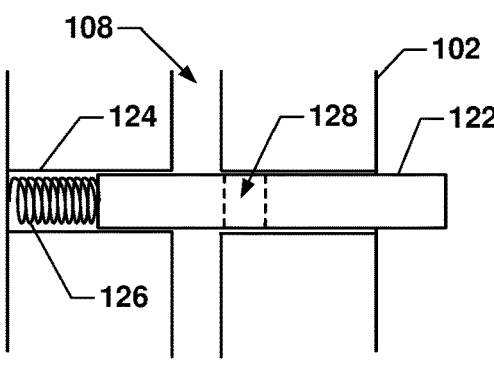
FIG. 1E
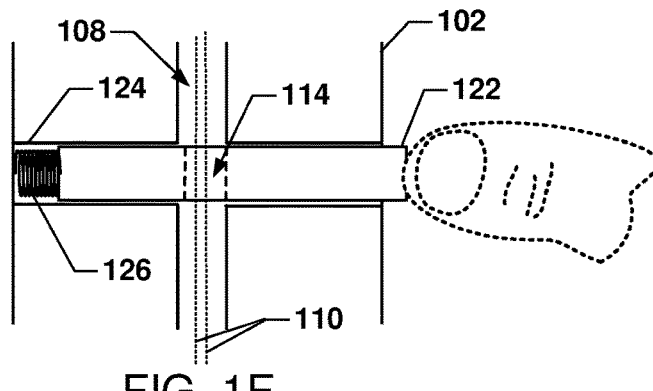
FIG. 1F
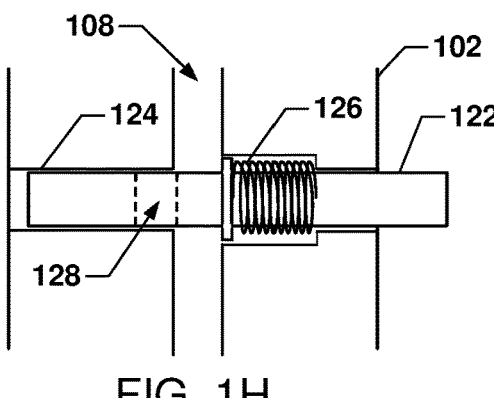
FIG. 1G
FIG. 1H

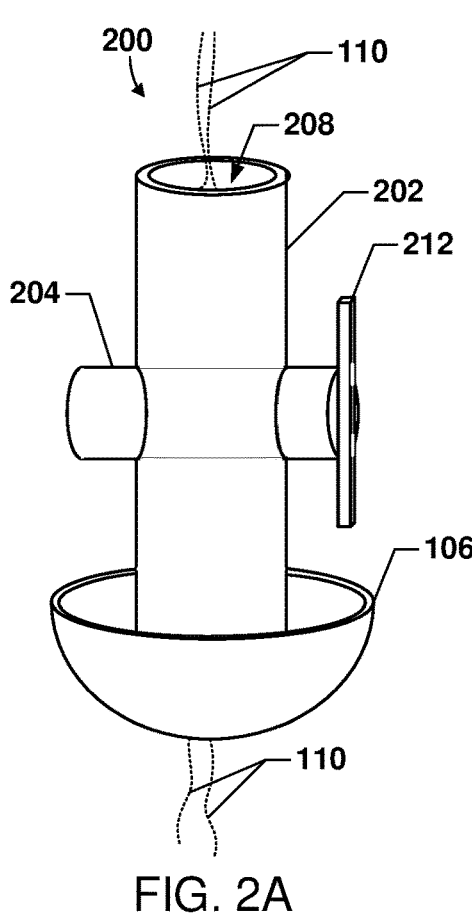
FIG. 2A
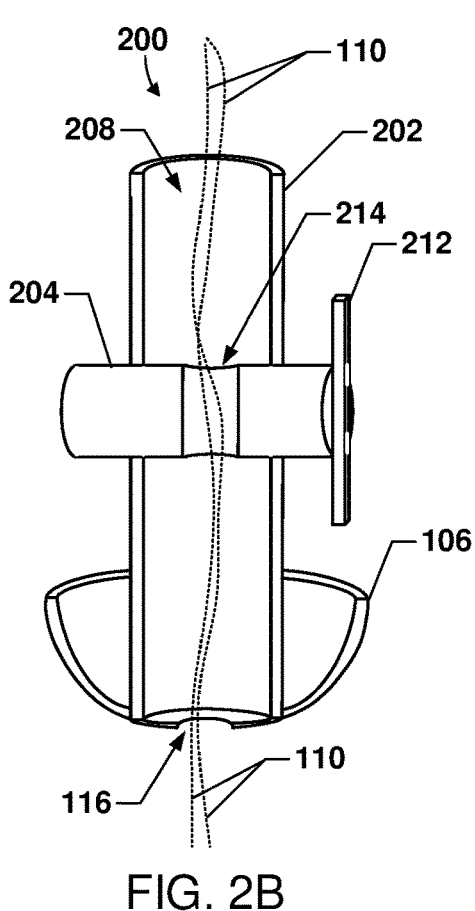
FIG. 2B
FIG. 2C

500

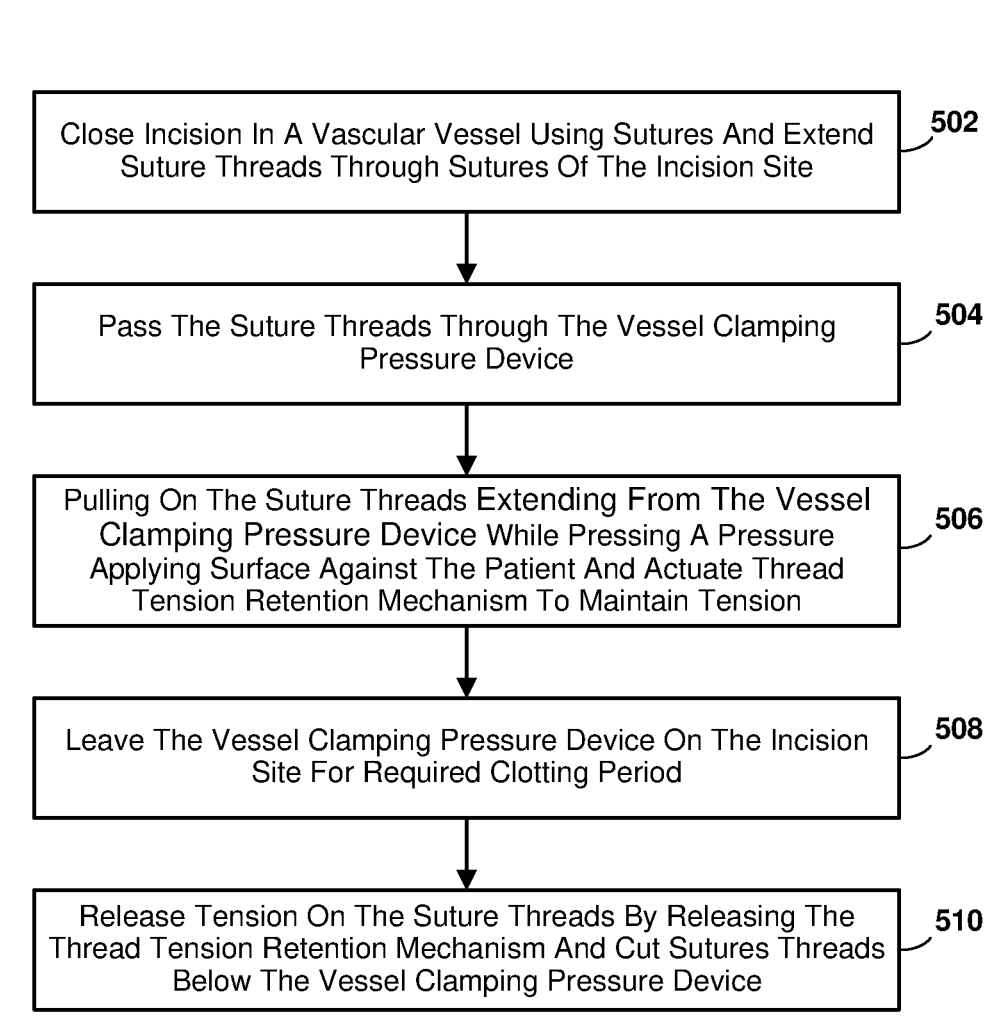

Close Incision In A Vascular Vessel Using Sutures And Extend Suture Threads Through Sutures Of The Incision Site ⌐502

Pass The Suture Threads Through The Vessel Clamping Pressure Device ⌐504

Pulling On The Suture Threads Extending From The Vessel Clamping Pressure Device While Pressing A Pressure Applying Surface Against The Patient And Actuate Thread Tension Retention Mechanism To Maintain Tension ⌐506

Leave The Vessel Clamping Pressure Device On The Incision Site For Required Clotting Period ⌐508

Release Tension On The Suture Threads By Releasing The Thread Tension Retention Mechanism And Cut Sutures Threads Below The Vessel Clamping Pressure Device ⌐510

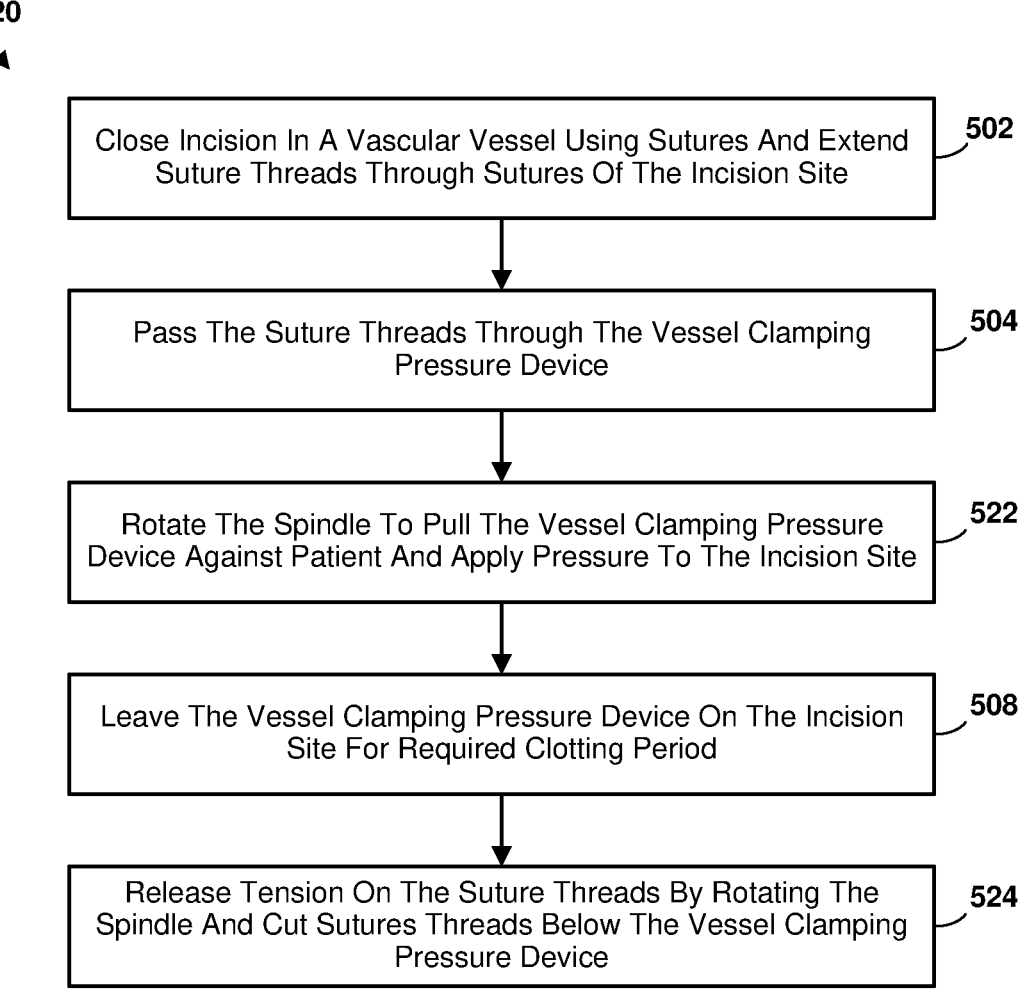

Close Incision In A Vascular Vessel Using Sutures And Extend Suture Threads Through Sutures Of The Incision Site — 502

Pass The Suture Threads Through The Vessel Clamping Pressure Device — 504

Rotate The Spindle To Pull The Vessel Clamping Pressure Device Against Patient And Apply Pressure To The Incision Site — 522

Leave The Vessel Clamping Pressure Device On The Incision Site For Required Clotting Period — 508

Release Tension On The Suture Threads By Rotating The Spindle And Cut Sutures Threads Below The Vessel Clamping Pressure Device — 524

FIG. 5B

SURGICAL VESSEL CLOSING PRESSURE DEVICE

RELATED APPLICATION

This application claims the benefit of priority to U.S. Provisional Patent Application 63/314,030 entitled "SURGICAL VESSEL CLOSING PRESSURE DEVICE" filed Feb. 25, 2022, the entire contents of which are hereby incorporated by reference for all purposes.

BACKGROUND

Currently, there are a number of medical procedures that involve inserting a catheter through the skin into a vascular vessel (e.g., a vein or artery) to gain access to various organs in the body. In such procedures, the skin is cut and the vessel is "cut down", allowing an introducer port to be inserted. Through this port, a catheter can be inserted. The most common procedures inserting a catheter into a vascular vessel are cardiac electrophysiology procedures and structural heart procedures. Examples of structural heart procedures involve inserting an artificial heart valve or a left atrial appendage closure device through a percutaneous access in the femoral artery.

A challenge faced in medical procedures including vascular vessel percutaneous access involves closing up the vessel and the incision site in the skin once the catheter and introducer are pulled out. Products have been designed to address this challenge, and can be utilized during the procedure. One such device is called "Perclose®", and is marketed by Abbott Laboratories, Inc., while another more recently introduced device labeled for both arterial and venous access sites is called "Vascade®" marketed by Cardiva Medical, Inc., a unit of Haemonectics Corporation.

While such vascular closure products assist in the closure process, one significant problem remains, which is continual bleeding at the insertion site. Such bleeding is compounded in some cases by anticoagulant therapy that some patients take as a routine therapy. To address this problem, a care giver must stay with the patient until the bleeding has stopped. Pressure is applied to the site, with some weighted bags, or most often by the care giver applying pressure with two or three fingers, for a time period of twenty minutes or more. The patient cannot be moved off the surgery table and to the recovery area during this time. As a result, the surgery room is occupied after surgery is completed, resulting in potentially less procedure throughput during any one day.

SUMMARY

Various embodiments include devices for applying continued pressure to vascular vessel (e.g., an artery or vein) following intravascular procedure. Various embodiments may include a pressure applying surface coupled to a mechanism for maintaining tension on suture threads extending from the closure of the vascular vessel.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments.

FIGS. 1E-1H are cross-sectional views of a vessel clamping vessel clamping pressure device showing an alternative configuration of a suture thread clamping mechanism according to some embodiments.

FIG. 2A is a perspective view of a vessel clamping pressure device according to some embodiments.

FIG. 2B is a cross-sectional view of a vessel clamping vessel clamping pressure device according to some embodiments.

FIG. 2C is a perspective view of a vessel clamping pressure device according to another embodiment.

FIGS. 5A and 5B are process flow diagrams of example methods for using a vessel clamping pressure device according to some embodiments.

DETAILED DESCRIPTION

Figure 1A:
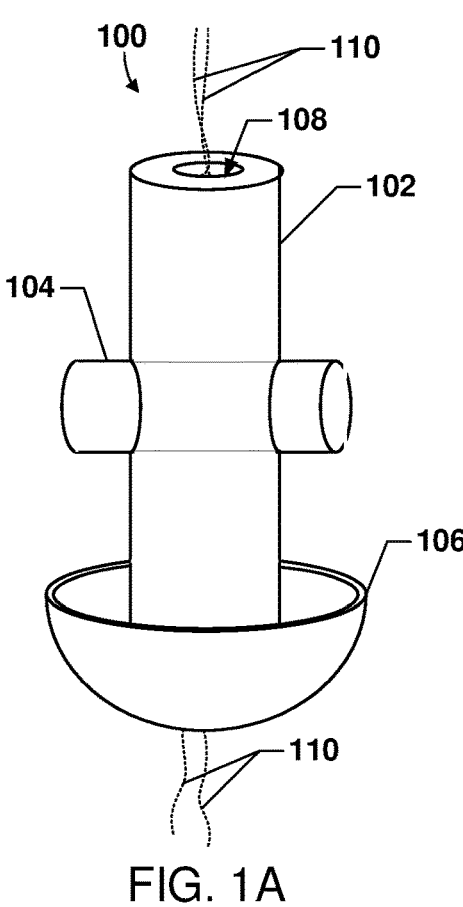
FIG. 1A is a perspective view of a vessel clamping pressure device according to some embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

In overview, various embodiments include a vessel clamping pressure device that can apply tension to suture threads that have been used to close the vascular vessel, thereby bring the pressure device in physical contact with the patient's skin sufficient to apply clamping pressure to the vessel stitches. Vessel clamping pressure devices according to various embodiments enable mechanical pressure to be provided to the closure of sutures in the a vascular vessel to prompt clotting and stop bleeding from the vessel, and obviate the need for a caregiver to spend extra time with the patient following closure. In addition to providing effective pressure on the vessel sutures, the device may enable the patient to be moved out of the surgery room to the recovery area sooner than when pressure is applied by caregivers or external weights.

To close up a vascular vessel and incision site, typically a threaded suture is run through or around the vessel, most often in a figure eight type threading, with the proximal and distal portions of the thread left outside the skin to tie off. In various embodiments, rather than tie off and cutting the suture threads, the suture threads are passed through a vessel clamping pressure device, including through a suture thread tensioning mechanism that maintains the pull on the suture threads to apply a clamping pressure to the patient's skin and thus to the closure the stitches in the vascular vessel.

Vessel clamping pressure devices of various embodiments may include a pressure applying surface coupled to a shaft that includes a mechanism for maintaining tension on suture threads so that the pressure-applying surface presses against the skin of the patient. The surface area of the pressure-applying surface of the surgical device may be one to two inches square, roughly consistent with the area of a caregiver's fingers that conventional apply pressure to the incision site after closure. The pressure-applying surface may include a passageway, such as a hole or slit, in the bottom side through which the suture threads can be passed. The pressure-applying surface may have a shape selected to match a contour of the patient's skin at the site of the incisions. For example, the pressure-applying surface may have a rounded or spherical shape to fit within a depression in the patient's body at the site of the incisions. As another example, the pressure-applying surface may have a flat, cylindrical or ellipsoidal shape to match various contours of the patient's body at the site of the incisions.

In some embodiments of vessel clamping pressure devices, the suture thread tensioning mechanism may include a suture thread clamping mechanism that a clinician can manipulate to maintain tension applied to the suture threads between the vascular vessel and the vessel clamping pressure device. In such embodiments, the suture thread tightening mechanism may include a thread gripping mechanism configured to maintain tension on suture threads after a clinician pulls the threads tight. In such embodiments, the clinician may pass the suture threads through the vessel clamping pressure device (e.g., before or after suturing the vascular vessel), pull the suture threads to tension the threads while sliding the device down the threads and against the patient's skin, and then activating the thread gripping mechanism to maintain the tension in the threads. Tensioning the suture threads and holding the threads taught via the thread gripping mechanism causes the pressure-applying surface to press against the skin of the skin of the patient, thereby applying clamping pressure to the closure of the stitches in the vascular vessel. Different thread gripping mechanisms may be used, such as a rotating clamping mechanism and a sliding clamping mechanism as described herein with reference to FIGS. 1A-1I.

Figure 2D:
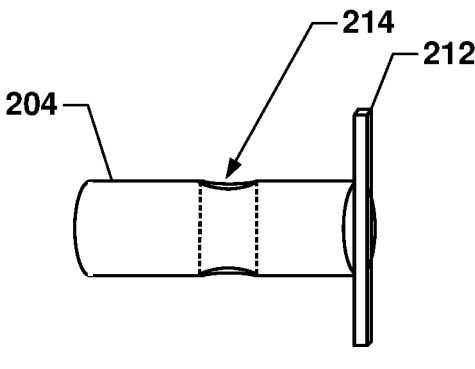
FIGS. 2D-2I are perspective views of alternative configurations a spindle for a vessel clamping pressure device according to some embodiments.
Figure 2E:
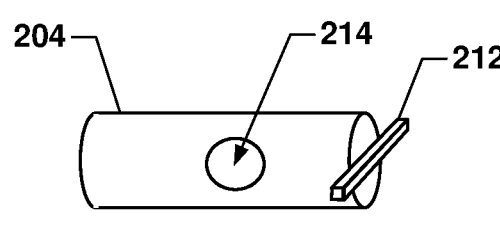
Figure 2F:
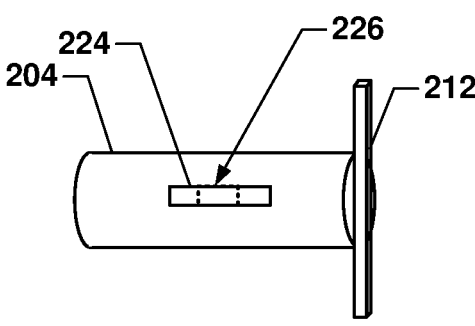
Figure 2G:
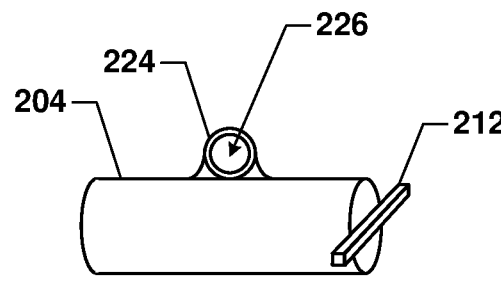
Figure 2H:
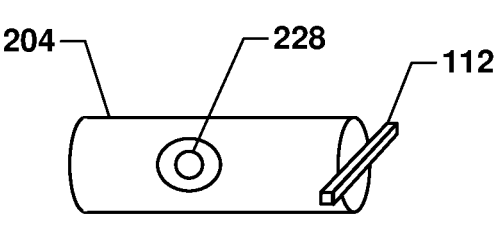
Figure 2I:
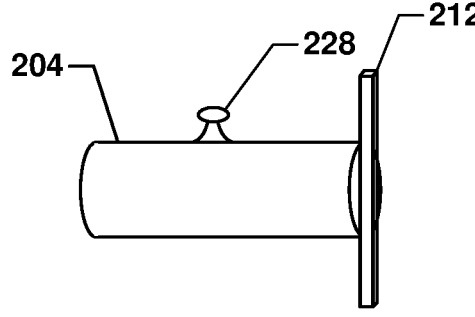
Figure 3:
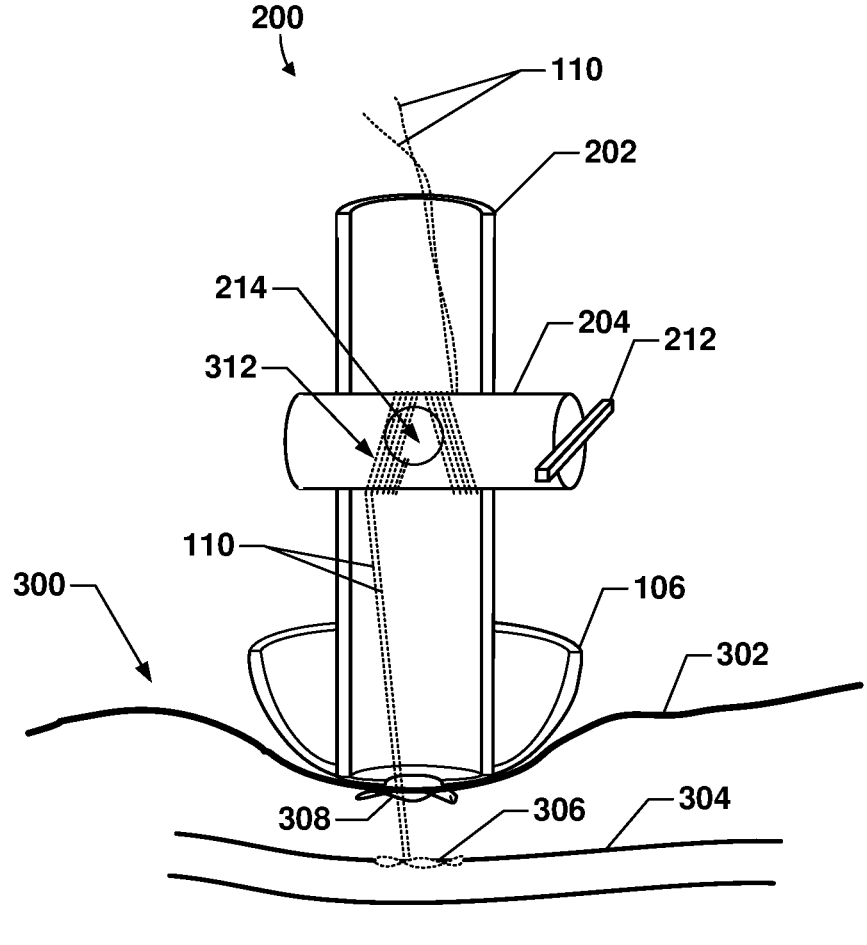
FIG. 3 is a cross-sectional view of a vessel clamping pressure device illustrating use on a patient according to some embodiments.

In some embodiments, the thread gripping mechanism may be in the form of a suture thread tightening mechanism coupled to the shaft that a clinician can manipulate to tension the suture threads between the vascular vessel and the vessel clamping pressure device as described herein with reference to FIGS. 2A-3. In such embodiments, the suture thread tightening mechanism may include a spindle within or coupled to a central shaft, with the spindle including a structure for engaging suture threads, such as a passageway (e.g., a hole or slit) through which suture threads may pass when the passageway is aligned with the lumen of the central shaft. The spindle may include or be coupled to a handle that can be turned to rotate the spindle, thereby binding the suture threads or rolling up slack in and applying tension to the suture threads connect to the vascular vessel.

The spindle and/or the shaft may include a feature or mechanism that resists or prevents turning or unreeling of the spindle (e.g., friction, a ratchet, etc.) In some uses, a clinician may pull on the suture threads to take up any slack in the suture threads, slide the vessel clamping pressure device into contact with the patient's skin, and then rotate the spindle to bind to maintain tension on the suture threads or take up slack in the suture threads to apply further tension to the suture threads between the device and the vascular vessel. In some uses, a clinician may not need to pull on the suture threads, by turning the spindle to take up slack in the threads and then apply a suitable amount of tension. Tensioning the suture threads in this manner causes the pressure-applying surface to press against the skin of the patient, thereby applying clamping pressure to the incision site and the stitches in the vascular vessel.

The various embodiment vessel clamping pressure devices may be configured as a single use disposable device, which may be sealed in sterile packaging before use.

FIG. 1A shows an example of a vessel clamping pressure device 100 according to some embodiments. As illustrated, a vessel clamping pressure device may include a central shaft 102 that includes a thread clamping mechanism 104 and that is coupled to a pressure applying surface 106. The central shaft 102 may include a passageway in the form of a lumen 108 through which suture threads 110 may be passed. The thread clamping mechanism 104 may be configured to enable a clinician to engage the thread clamping mechanism so as to maintain tension in the suture threads 110 leading to the stitches in a vascular vessel.

In various embodiments, the area of the pressure applying surface 106 that contacts the skin of a patient may be approximately 1 to 2 square inches. As described in more detail herein, the pressure applying surface 106 may have an external contour that is selected to match a typical contour of a patient's body at a location of an intravascular incision. For example, the pressure applying surface 106 of the embodiment illustrated in FIG. 1A is hemispherical in shape so as to fit the contours of the thigh at the location where a cardiac catheter may be inserted in the femoral artery of a typical patient. As discussed below with reference to FIGS. 4B, 4C and 4D, the pressure applying surface 106 may be of different shapes or contours, including flat, spherical, ellipsoidal, and irregular. In some embodiments, vessel clamping pressure devices 100 may be produced with different shaped pressure applying surfaces 106 to enable clinicians to select a suitably shaped model for use on a patient depending upon the location and surface contour of the incision site for a particular patient. In some embodiments, the vessel clamping pressure device 100 may be configured so that different shaped pressure applying surfaces 106 may be attached to a common shaft 102, enabling clinicians to select an appropriately shaped pressure applying surface depending on the location and surface contour of the incision site for a particular patient.

Figure 1B:
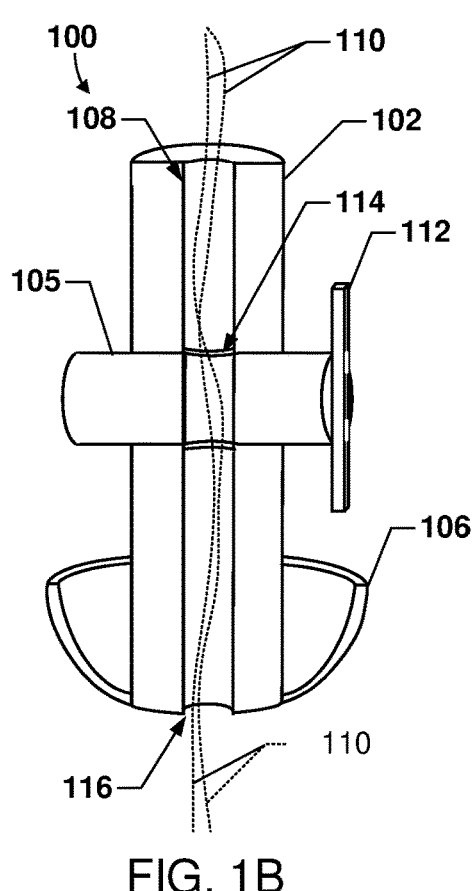
FIGS. 1B and 1C are cross-sectional views of a vessel clamping vessel clamping pressure device according to some embodiments.
Figure 1C:
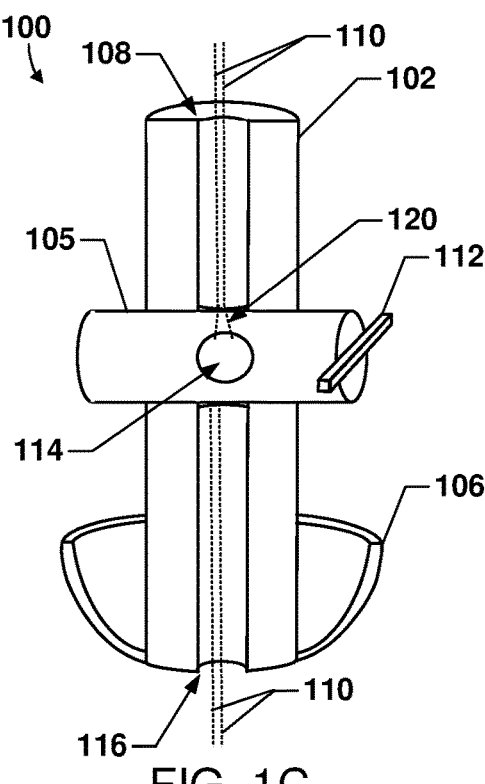
Figure 1D:
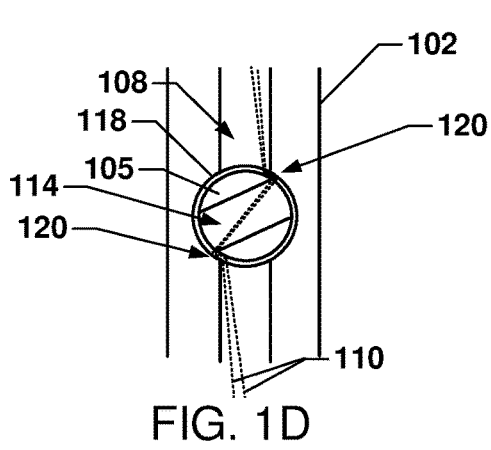
FIG. 1D is a cross-sectional view of the embodiment of a vessel clamping pressure device illustrated in FIG. 1C showing a portion of the device from a different viewing angle.

The shaft 102 may include a chamber for receiving the thread clamping mechanism 104. As mentioned, the thread clamping mechanism 104 may be any of be a variety of forms. FIGS. 1B-1D illustrate a non-limiting example of a thread clamping mechanism 104 in the form of a rotating spindle 105 with a passageway in the form of a hole 114, that will enable suture threads to pass through device when the spindle 105 is rotationally oriented so that the hole is aligned with the lumen 108, and jam or grip suture threads when the spindle is rotated within a complementary volume within the shaft 102 into a rotational orientation in which the hole is misaligned with the lumen. FIGS. 1E-1H illustrate a non-limiting example of a thread clamping mechanism 104 in the form of a spring-biased translating bar 122 with a passageway in the form of a hole 114 through which suture threads 110 can pass when the translating bar is depressed or pulled out so that the hole aligns with the lumen 108 and that will jam or grip suture threads against a portion of the shaft 102 when the translating bar is released so that the hole misaligns with the lumen 108.

FIGS. 1B-1D shows cross-sectional views of the embodiment of a vessel clamping pressure device 100 in which the thread clamping mechanism 104 includes a spindle 105 with a passageway in the form of a hole 114 sized to receive suture threads 110 and uses rotation to misalign the hole 114 with the lumen and press suture threads against a complementary surface in the shaft 102 and thus grip the threads so as to maintain tension on the threads. As illustrated in FIG. 2B, suture threads 110 may be passed through a passageway in the form of an opening 116 in the pressure applying surface 106, through the lumen 108 in the central shaft 102, and through the hole 114 within the spindle 105 when the spindle is rotationally oriented so that the hole aligns with the lumen. The passageway in the form of opening 116 in the pressure applying surface 106 may have a smaller diameter than the diameter of the lumen 108 of the shaft 102 so as to provide even pressure to the skin of the patient.

As illustrated in FIGS. 1C and 1D, rotating the spindle 105, rotates the hole 114 out of line (i.e., misaligned) with the lumen 108, pulling the suture threads 110 into engagement (shown with arrows 120) with a complementary surface 118 in the shaft 102. As illustrated in FIG. 1D, the complementary surface 118 may be in the form of a circular cavity with a diameter that is approximately equal to the diameter of the thread clamping mechanism 104 plus two times the diameter of suture threads. Thus, rotating the spindle 105 causes the suture threads 110 to be pressed between the spindle 105 and the complementary surface 118, thereby providing a clamping force that maintains tension on the threads between the pressure applying surface 106 and the vascular vessel.

Passing the suture threads 110 through a passageway in the form of hole 114 in a spindle 105 of the thread clamping mechanism 104 provides a simple mechanism for gripping the threads by rotating the spindle.

In the embodiment illustrated in FIGS. 1E-1G, the thread clamping mechanism 104 includes a spring-biased translating bar 122 that is positioned within a chamber 124 in the shaft 102 that intersects the lumen 108. The translating bar 122 may be long enough to extend beyond one side of the shaft 102. As illustrated in FIG. 1E, a spring 126 in the chamber 124 may bias the translating bar 122 so that the hole 114 in the member is normally misaligned with the lumen 108.

Referring to FIG. 1F, to pass suture threads 110 through the vessel clamping pressure device 100, such as before suturing or after closing the incision site, a clinician may press the portion of the translating bar 122 extending beyond the surface of the shaft 102, compressing the spring 126 and aligning a passageway in the form of the hole 114 in the translating bar 122 with the lumen 108 in the shaft. In this configuration, the suture threads 110 can be passed up through the opening 116 in the pressure applying surface 106, through the lumen 108 in the shaft 102, through the hole 114 within the translating bar 122 and out the top of the vessel clamping pressure device 100.

To apply pressure to the incision site, the clinician may pull on the suture threads to take up any slack as illustrated in FIG. 1F and press the vessel clamping pressure device 100 against the skin of the patient. Then to maintain pressure on the incision site, the clinician releases the translating bar 122, permitting the spring 126 to slide the member toward its non-depressed position, which misaligns the hole 114 in the member with the lumen 108 of the shaft securing the suture threads 110 as illustrated in FIG. 1G. As illustrated, sliding the translating bar 122 to misalign the hole 114 in the member with the lumen 108 of the shaft 102 binds the suture threads 110 passing through the hole between the translating bar and the chamber 124.

To release the tension on the suture threads 110, such as to remove the vessel clamping pressure device 100 after a suitable period of pressure on the incision site, the clinician may again press the portion of the translating bar 122 extending beyond the surface of the shaft 102, compressing the spring 126 and aligning the hole 114 in the translating bar 122 with the lumen 108 in the shaft as illustrated in FIG. 1F.

In an alternative embodiment illustrated in FIG. 1H, the translating bar 122 may be spring loaded in a manner opposite to that illustrated in FIGS. 1E-1G such that the spring 126 is oriented to resist a pulling action on the translating bar. In this embodiment, a clinician may pull (rather than push as illustrated in FIG. 1F) the translating bar to align a passageway in the form of a hole 128 with the lumen 108 in the shaft 102 for passing suture threads through the vessel clamping pressure device 100. In this embodiment, pulling on the translating bar 122 compresses the spring 124, which provides force to return the translating bar to the illustrated position in which the hole 128 is misaligned with the lumen 108, thus binding the suture threads 110 passing through the passageway in the form of a hole 128 between the translating bar and the chamber 124 in a manner similar to the illustration in FIG. 1G.

In the embodiment illustrated in FIG. 1H, a clinician may pull on the translating bar 122 to pass suture threads through the vessel clamping pressure device 100 and press the device against the patient's skin while tensioning the threads with one hand, and then release the translating bar to maintain the tension on the suture threads and thus the clamping force on the sutured incisions. To remove the vessel clamping pressure device 100, the clinician may pull on the translating bar 122 to align the hole 114 with the lumen 108, enabling the suture threads 110 to pass through the hole, releasing the tension and enabling the threads to be removed from the device.

In various embodiments, the length of the shaft 102 above the spindle 104 or translating bar 122 may vary from the relative amount illustrated in the figures. For example, the shaft 102 may end just above the spindle 104 or translating bar 122. Further, in some embodiments, the length of the shaft 102 between the spindle 104 or translating bar 122 and the pressure applying surface 106 may vary from the relative amount illustrated in the figures. For example, the distance between the spindle 104 or translating bar 122 and the pressure applying surface 106 may be just long enough to permit actuation of the thread clamping mechanism 104.

FIGS. 2A-2I shows an example of a vessel clamping pressure device 200 according to some further embodiments. As illustrated, a vessel clamping pressure device 200 according to such embodiments may include a central shaft 202 that includes a rotatable spindle 204 and that is coupled to the pressure applying surface 106. Similar to the embodiments illustrated in FIGS. 1A-1G, the area of the pressure applying surface 106 that contacts the skin of a patient may be approximately 1 to 2 square inches and have an external contour that is selected to match a typical contour of a patient's body at a location of an intravascular incision.

The central shaft 202 may include a passageway in the form of a lumen 208 through which suture threads 110 may be passed. The spindle 204 may include a handle 212 or other structure that enables a clinician to rotate the spindle so as to tension (or maintain tension on) suture threads 110 leading to the stitches in a vascular vessel. The shaft 202 may include an opening for receiving the spindle 204 and allowing the spindle to be rotated about its long axis. The shaft 202 and/or the spindle 204 may further include a mechanism (not shown separately) for limiting unwinding of the spindle after the suture threads have been tightened. Any of a variety of unwinding limiting mechanism may be used, including friction between spindle and the shaft, a ratchet mechanism that permits rotation in one direction but not the other, a tooth and gear interface that permits rotation of the spindle when pushed in but resists rotation when released, etc.

FIG. 2B shows a cross-sectional view of the embodiment of a vessel clamping pressure device 200 shown in FIG. 2A. As illustrated, suture threads 110 may be passed through a passageway in the form of an opening 116 in the pressure applying surface 106, through the lumen 208 in the central shaft 202, and through a hole 214 within the spindle 204. The passageway or opening 116 in the pressure applying surface 106 may have a smaller diameter than the diameter of the lumen 208 of the shaft 202 so as to provide even pressure to the skin of the patient.

Passing the suture threads 110 through the hole 214 in the spindle 204 provides a simple mechanism for coupling the threads to the spindle so that when the spindle is rotated, the suture threads between the spindle and the vascular vessel are tightened as illustrated in FIG. 3.

In various embodiments, the length of the shaft 202 above the spindle 204 may vary from the relative amount illustrated in the figures. For example, the shaft 202 may end just above the spindle 204. Further, in some embodiments, the length of the shaft 202 between the spindle 204 and the pressure applying surface 106 may vary from the relative amount illustrated in the figures. For example, the distance between the spindle 204 and the pressure applying surface 106 may be just long enough to accommodate windings of the suture threads 110 about the spindle 204.

In some embodiments, the shaft 202 may not be tubular as illustrated in the drawings, and instead may be any of a variety of structures that supports the spindle 204 and connects to the pressure applying surface 106. For example, as illustrated in FIG. 2C, the shaft 210 may be a solid rod coupled to one or more bearings 218, 220 via a support structure 222, with the bearings 218, 220 configured to provide rotational support for the spindle 204. In such an embodiment, the suture threads 110 may pass through a passageway in the form of the opening 116 in the pressure applying service 106 and through a passageway in the form of the hole 214 in the spindle 204 without passing through a lumen in the shaft 210. In some embodiments, the shaft 210 may be shorter relative to the pressure apply surface 106 than illustrated, and configured to support the bearings 218, 220 on the pressure apply surface 106 to enable rotation of the spindle 204.

The spindle 204 may include a variety of features for securing the suture threads 110 for winding. Three non-limiting alternatives are illustrated in FIGS. 2D-2I.

FIGS. 2D and 2E show an embodiment of a spindle 204 including a passageway in the form of a hole 214 through which suture threads 110 may be passed. In such embodiments, the hole 214 may have a diameter sufficient to receive the suture threads 110. In some embodiments, the hole 214 may have a diameter similar to or the same as the diameter of the lumen 208 in the shaft 202. Rotating the handle 212 on the spindle 204 (e.g., as shown in FIG. 2B) then causes the suture threads 110 to be wound about the spindle as illustrated in FIG. 3.

FIGS. 2F and 2G show an embodiment of a spindle 204 including a ring 224 or similar structure having a passageway in the form of a hole 226 through which suture threads 110 may be passed. In this embodiment, suture threads may be passed through the hole 226 when the spindle 204 is turned so that the ring 224 is oriented approximately perpendicular to the long axis of the shaft 202, which orients the axis of the hole 226 approximately parallel to the long axis of the shaft 202. Similar to the embodiments illustrated in FIG. 2A-2E, turning the spindle 204 will wrap suture threads 110 around the spindle in a manner similar to the example illustrated in FIG. 3.

FIGS. 2H and 2I show an embodiment of a spindle 204 having a structure, such as a knob 228 as illustrated, a hook, or similar structure, that may catch or secure suture threads 110 so that the threads will be wound around the spindle when it is rotated. For example, in an embodiment of a vessel clamping pressure device 200 in which the spindle 204 includes a knob 228, the suture threads 110 may be wound around the knob to secure the threads to the spindle before winding the spindle. Such an embodiment of the spindle 204 may be useful in a vessel clamping pressure device 200 embodiments with a solid shaft 210 as illustrated in FIG. 2C in which the knob 228 is not hidden from view or access within a lumen 208 of the shaft. With suture threads 110 wound around or otherwise connected to the knob 228 (or similar structure), turning the spindle 204 will wrap suture threads 110 around the spindle in a manner similar to the example illustrated in FIG. 3.

While not illustrated in FIGS. 1A-2I, a tool such as a straight needle may be used to push or pull the suture threads 110 through the passageway in the vessel clamping pressure device 100, 200, including through a hole 114 in the spindle 105, 204 or translating bar 122, which may be hidden from view depending upon the materials used in the central shaft 102. As another alternative, the suture threads 110 may be threaded through the passageway in the vessel clamping pressure device 100, 200 before (or in preparation for) the suture threads are used to stitch or otherwise close the incision in the vascular vessel.

FIG. 3 shows a cross-sectional view of an embodiment of a vessel clamping pressure device 200 in which the spindle 204 has been rotated a few turns, winding suture threads 110 around the spindle sufficient to tighten the suture threads 110 between the spindle 204 and the vascular vessel 304. As illustrated in FIG. 3, slack in the suture threads 110 between the spindle 204 and the vascular vessel 304 is taken up in windings 312 on the spindle. Tightening the suture threads 110 draws the vessel clamping pressure device 200 toward the vascular vessel 304, which causes the pressure applying surface 106 to press against the skin 302 of a patient 300 at the incision site closure 308. With suture threads 110 extending from the vascular vessel 304, such as from sutures 306 in the vessel, a clamping force may be induced between the vascular vessel 304 and the pressure applying surface 106 (and the patient's skin 302) that can stop or minimize bleeding and accelerate clotting at the site of the incision in the vessel without the need for a clinician to apply external pressure to the incision site closure.

A vessel clamping pressure device 100, 200 according to various embodiments may vary in form and structure from that illustrated in FIGS. 1A-3, some non-limiting examples of which are illustrated in FIGS. 4A-4D.

Figure 4A:
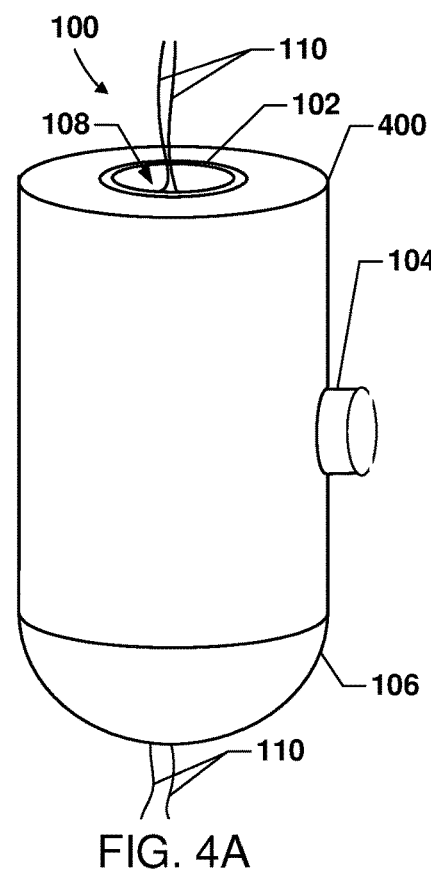
FIGS. 4A-4D are perspective views of some alternative configurations of a vessel clamping pressure device according to some embodiments.

For example, as illustrated in FIG. 4A, a vessel clamping pressure device 100, 200 may include a case or shell 400 that encompasses the central shaft 102, 202 fitting against the pressure applying surface 106. In some embodiments, the central shaft 102, 202 may have an outer diameter (or outer surface contour) that matches the pressure applying surface 106, in which case the central shaft 102, 202 would have the shape of the shell 400. By hiding surface contours that could harbor bacteria, such a configuration of a vessel clamping pressure device 100, 200 may facilitate sterilizing the device before packaging, as well as after use for devices configured for reuse (i.e., not single-use disposable models).

Figure 4B:
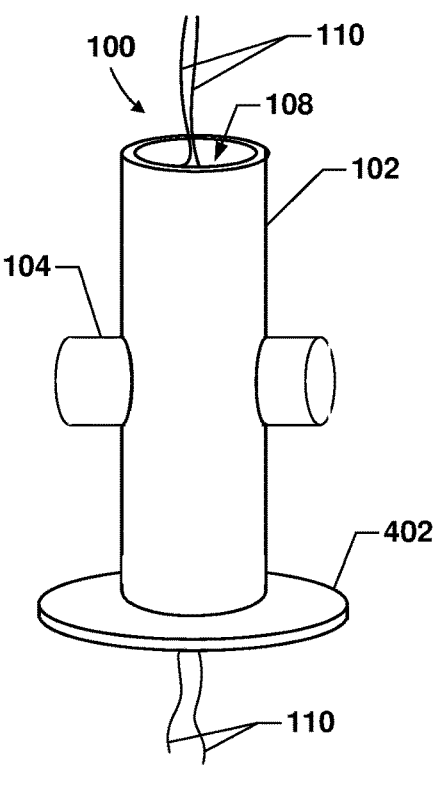
Figure 4C:
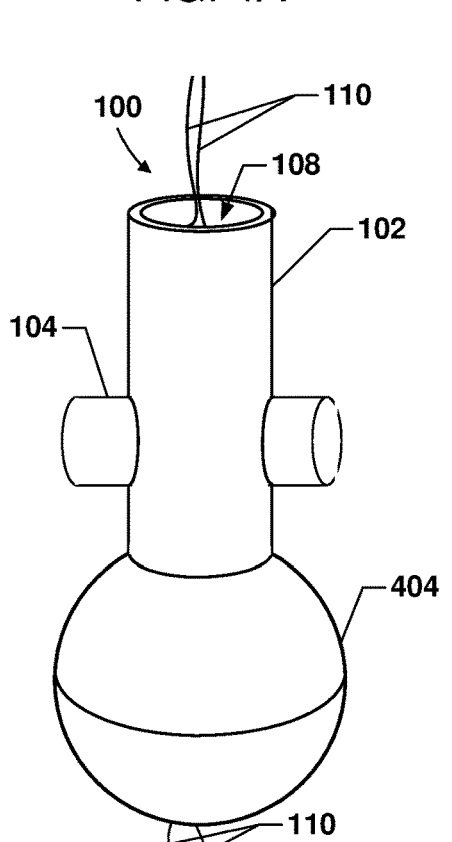
Figure 4D:
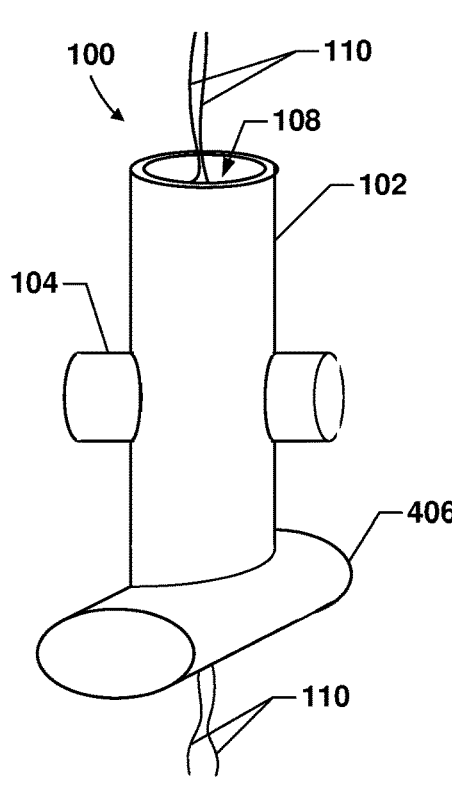

As noted above, the pressure applying surface 106 may have a variety of shapes and contours that may be selected to match the skin of the patient at the site of the incisions, some none limiting examples of which are illustrated in FIGS. 4B-4D. As illustrated in FIG. 4B, the pressure applying surface 402 may be flat or nearly flat, such as a disk having an area of approximately one to two square inches. As illustrated in FIG. 4C, the pressure applying surface may be a solid shape, such as a sphere 404, with a radius selected so that the portion of the solid shape that contacts a patient's skin has a surface area of approximately one to two square inches. As illustrated in FIG. 4D, the pressure applying surface may be a complex shape, such as an elongated ellipsoid 406, with major, minor and longitudinal axes selected so that the portion of the shape that contacts a patient's skin has a surface area of approximately one to two square inches.

FIG. 5A is a process flow diagram illustrating a method 500 for using a vessel clamping pressure device 100 according to some embodiments. With reference to FIGS. 1A-11, the method 500 may be performed as part of the closure of a vascular vessel following a catheterization procedure.

In block 502, a clinician may close the incision in a vascular vessel using sutures, and extend the suture threads (e.g., 110) through sutures of the entrance incision, which is then sutured close.

In block 504, a clinician may pass the suture threads (e.g., 110) through a passageway through the vessel clamping pressure device 100. As described herein, this operation may involve passing the suture threads through a hole 116 in the pressure applying surface (e.g., 106, 402, 404, 406), through a hole (e.g., 114, 228) in/on the thread clamping mechanism 104, and out the top of the vessel clamping pressure device 100. As described with reference to FIGS. 8-11, this operation may involve slipping the suture threads into slits that provide a passageway through the vessel clamping pressure device 800.

In block 506, a clinician may pull on the suture threads extending from the vessel clamping pressure device to tension the threads while pressing the vessel clamping pressure device against the patient to apply pressure to the incision site, and then actuate the thread tension retention mechanism (e.g., 104, 105, 122) to maintain the tension in the threads and thus the pressure against the incision site. As discussed herein, in some embodiments, actuating the thread tension retention mechanism may involve rotating a spindle (e.g., 105) with a hole (e.g., 114) through which the suture threads (e.g., 110) pass so as to grip the threads between the spindle and a corresponding surface in a shaft (e.g., 102) of the vessel clamping pressure device. Also as discussed herein, in some embodiments, tensioning the threads while pressing the vessel clamping pressure device against the patient in block 506 may include pressing or pulling on a translating bar (e.g., 122) to align a hole (e.g., 144) in the bar with a lumen (e.g., 108) in the shaft (e.g., 102) to enable the suture threads to pass through the hole, and actuating the thread tension retention mechanism may include releasing the translating bar to misalign the hole with the lumen to grip the threads between the translating bar and a chamber (e.g., 124) in the shaft of the vessel clamping pressure device.

In block 508, a clinician may leave the vessel clamping pressure device on the incision site for a required clotting period. At this point, the patient may be moved out of surgery, such as to recovery.

In block 510, after a sufficient period of time, a clinician may release tension on the suture threads by actuating the thread tension retention mechanism and cut the sutures threads below the vessel clamping pressure device. As discussed herein, in some embodiments, actuating the thread tension retention mechanism to release tension on the suture threads may involve rotating a spindle (e.g., 105) to align a passageway in the form of a hole (e.g., 114) in the spindle with the lumen in the shaft, allowing the threads to pass through the hole. Also as discussed herein, in some embodiments, actuating the thread tension retention mechanism to release tension on the suture threads may involve pressing or pulling on a translating bar (e.g., 122) to align a passageway in the form of a hole (e.g., 144) in the bar with the lumen in the shaft to enable the suture threads to pass through the hole.

After removal from the client, vessel clamping pressure devices configured as single-use disposable items may be disposed of.

FIG. 5B is a process flow diagram illustrating a method 520 for using a vessel clamping pressure device 200 according to some embodiments. With reference to FIGS. 2A-5B, the method 500 may be performed as part of the closure of a vascular vessel following a catheterization procedure.

In block 502, a clinician may close the incision in a vascular vessel using sutures, and extend the suture threads (e.g., 110) through sutures of the entrance incision, which is then sutured close.

In block 504, a clinician may pass the suture threads (e.g., 110) through a passageway in the vessel clamping pressure device 200. As described above, this operation may involve passing the suture threads through a hole 116 in the pressure applying surface (e.g., 106, 402, 404, 406), through a hole (e.g., 214, 228) in/on a spindle 204 (or engage a structure such as a knob 228 or hook on the spindle), and out the top of the vessel clamping pressure device 200. As described with reference to FIGS. 8-11, this operation may involve slipping the suture threads into slits that provide a passageway through the vessel clamping pressure device 800.

In block 522, a clinician may rotate the spindle to tension the suture threads between the spindle 204 and the vascular vessel, thereby pulling the pressure applying surface of the vessel clamping pressure device against the patient and applying pressure to the incision site. This operation may include engaging a mechanism to prevent the spindle from unwinding, such as engaging a ratchet or tightening a tension nut the spindle.

In block 508, a clinician may leave the vessel clamping pressure device on the incision site for a required clotting period. At this point, the patient may be moved out of surgery, such as to recovery.

In block 524, after a sufficient period of time, a clinician may release tension on the suture threads by rotating the spindle to unwind threads and cut the sutures threads below the vessel clamping pressure device.

After removal from the client, vessel clamping pressure devices configured as single-use disposable items may be disposed of.

Figure 6:
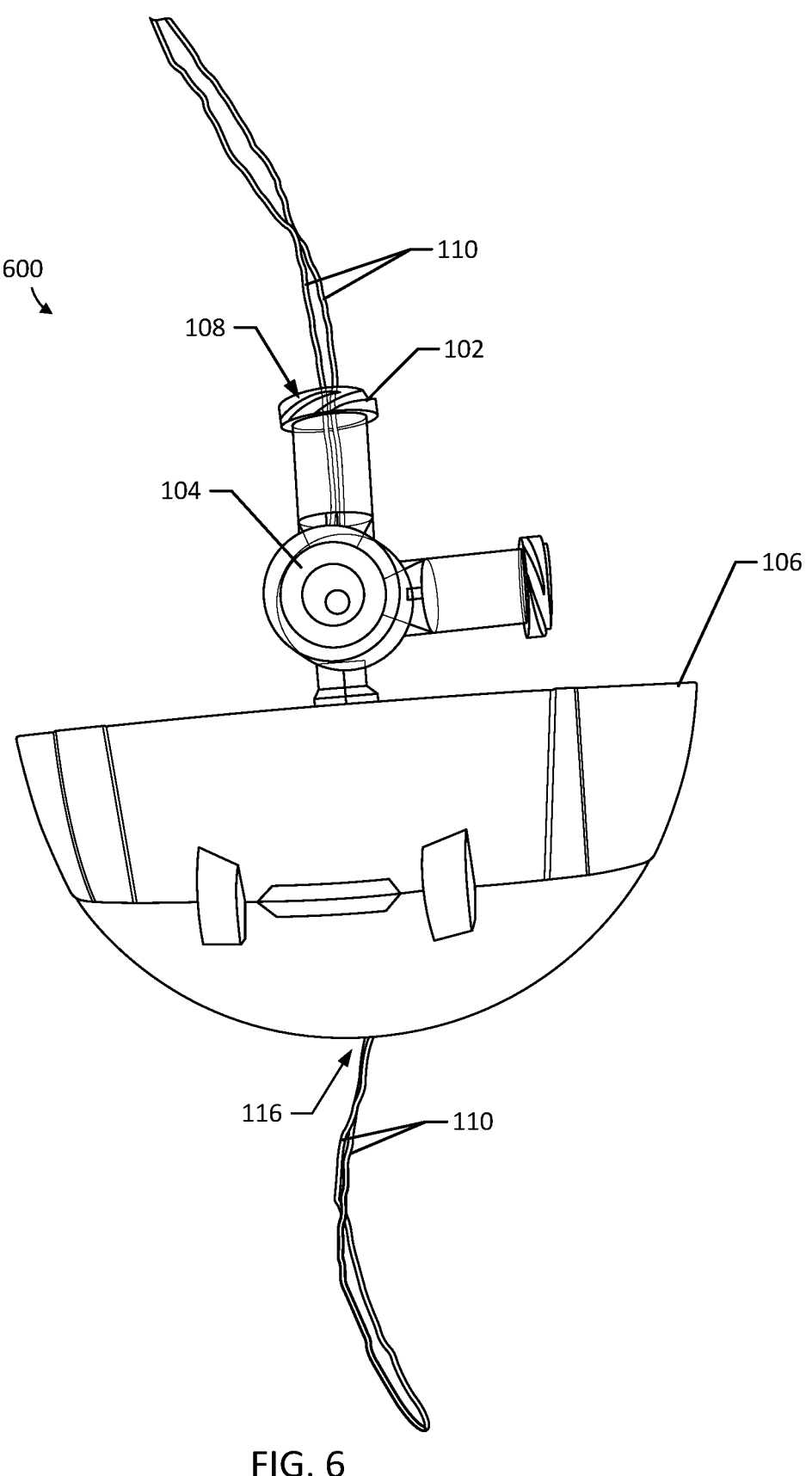
FIGS. 6 and 7 are perspective views of a prototype vessel clamping pressure device according to some embodiments.
Figure 7:
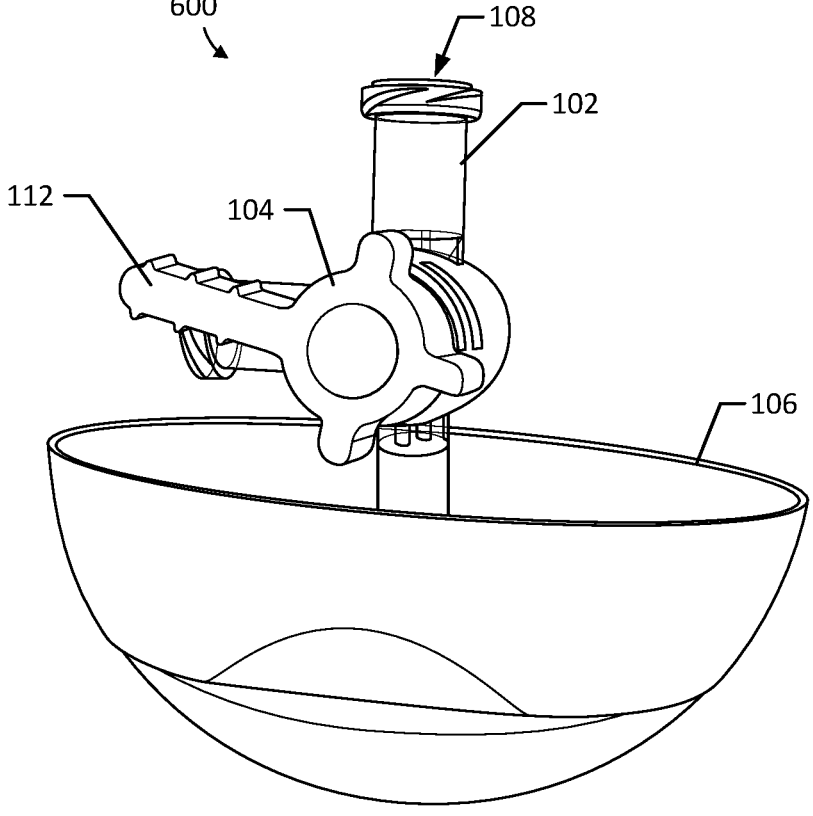
Figure 8:
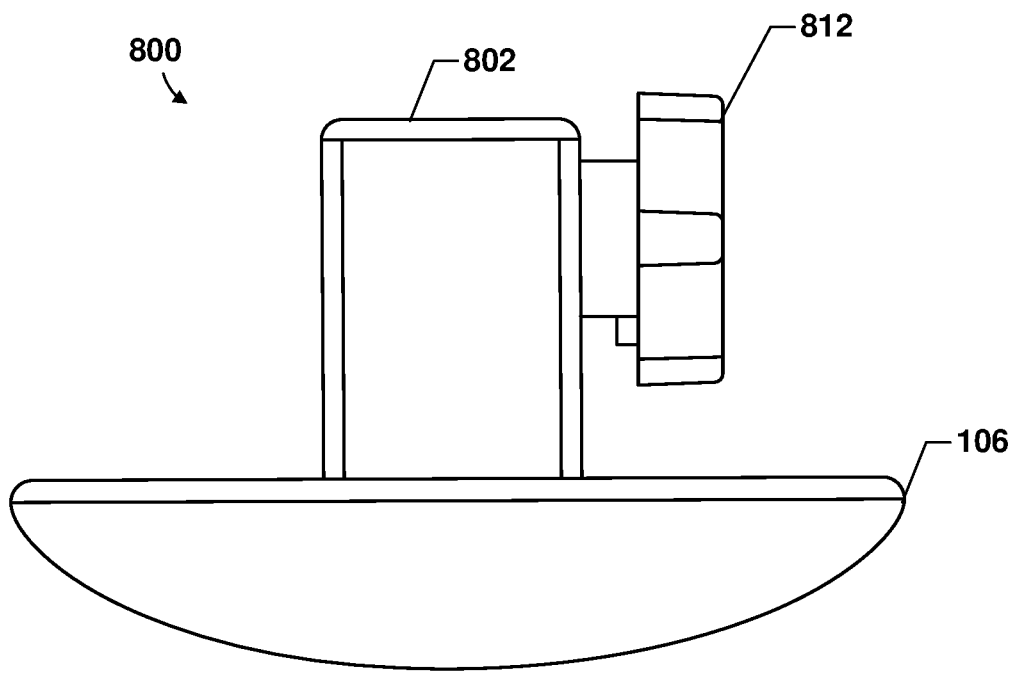
FIG. 8 is a side view of a vessel clamping pressure device according to another embodiments.

FIGS. 6 and 7 are illustrations of a prototype vessel clamping pressure device 600 according to a non-limit embodiment. In this prototype, a stopcock is used for the shaft 102 and spindle 104. FIG. 6 shows one side of the prototype clamping pressure device 600 with suture threads 110 passing through the lumen 108 within the valve body, through the spindle 104 (i.e., through the hole in the valve plug) and through an exit hole 116 in the hemispherical pressure applying surface 106. As described herein, when the spindle 104 (i.e., the valve plug) is rotated, the suture threads 110 will wrap around the spindle, thus tightening (or maintaining tension on) the suture threads between the pressure applying surface 106 and the patient. FIG. 7 shows the other side of the prototype clamping pressure device 600 from an angle that shows the handle 112 of the spindle 104 (i.e., the valve plug).

FIGS. 8-11 are illustrations of another embodiment of a vessel clamping pressure device 800. Like other embodiments, the vessel clamping pressure device 800 may include a central shaft 802 coupled to the pressure applying surface 106. In the embodiment illustrated in FIGS. 8-11, the central shaft 802 may have a rectangular cross section as illustrated, or other configuration. In some embodiments, the central shaft 802 may be glued, fused or otherwise firmly coupled to the pressure applying surface 106. In some embodiments, the central shaft 802 and the pressure applying surface 106 may be manufactured as a single structures, such as in a single mold or using additive manufacturing technologies (known as 3D printing).

Figure 11:
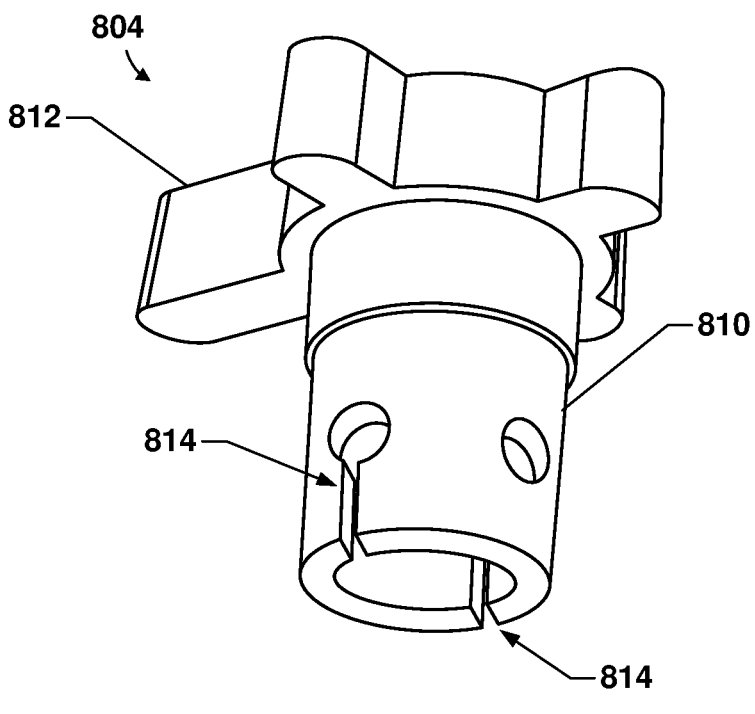
FIG. 11 is perspective view of a spindle component of the vessel clamping pressure device of the embodiment shown in FIG. 8.

A spindle 804 may fit into the central shaft 802 and be configured to turn within the shaft. The spindle 804 may include a handle 812 to facilitate turning the spindle 804. As illustrated in FIG. 11, the spindle 804 may include an interior portion 810 that fits within the central shaft 802 and includes slits 814 that form a spindle passageway through which sutures may be passed.

Figure 9:
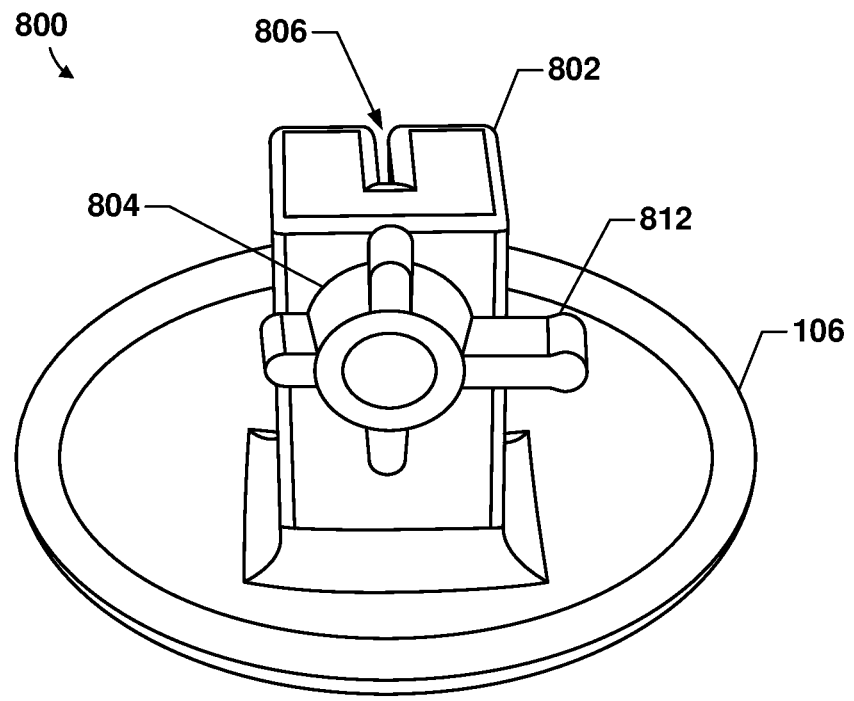
FIGS. 9 and 10 are perspective views of the vessel clamping pressure device of the embodiment shown in FIG. 8.
Figure 10:
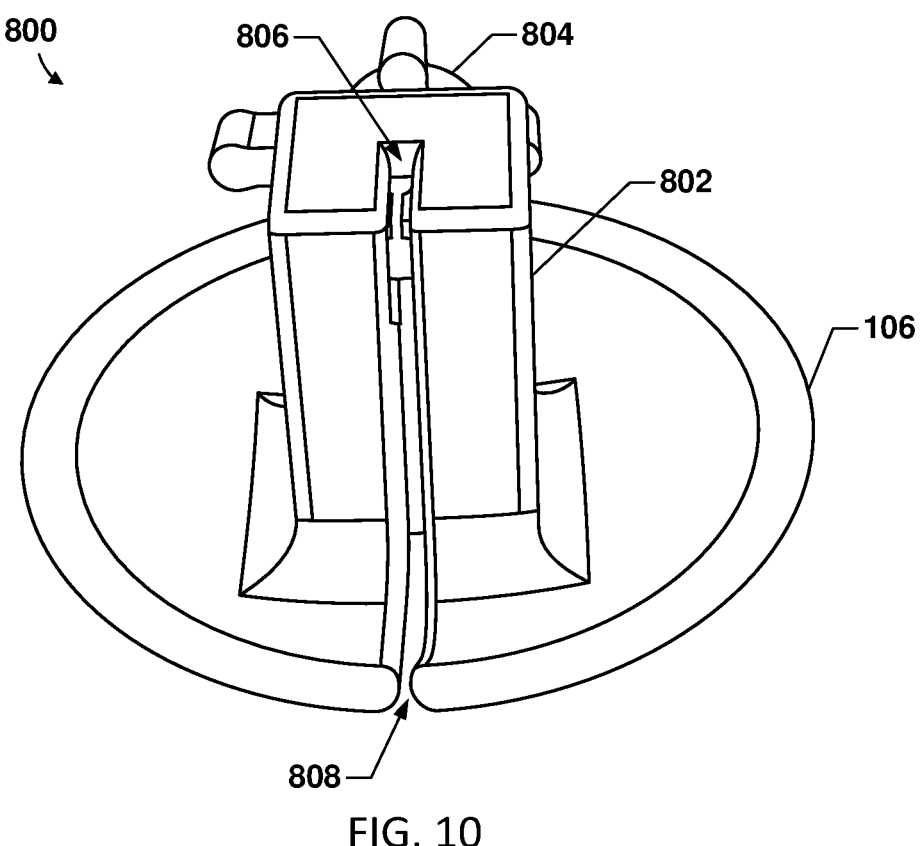

As illustrated in FIGS. 9 and 10, the central shaft 802 may include a passageway in the form of a slit 806 that matches up with a passageway in the form of a slit 808 in the pressure applying surface 106. The passageway slits 806, 808 in the central shaft 802 and the pressure applying surface 106 provide a passageway for sutures through the vessel clamping pressure device 800. The passageway in the form of a slit 808 in the central shaft 802 may be sized to match up with the spindle passageway in the form of slits 814 in the interior portion 810 of the spindle 804 when the spindle is positioned within the central shaft. The passageway slits 806, 808 and 814 in the central shaft 802, pressure applying surface 106 and spindle interior portion 810 enable the vessel clamping pressure device 800 to be attached to sutures without having to thread the sutures through an interior passage as in other embodiments described herein.

To connect the vessel clamping pressure device 800 to sutures, a clinician may turn the spindle 804 to align the spindle passageway slits 814 in the interior portion 810 with the slits 806, 808 in the central shaft 802 and pressure applying surface 106, and then slip the sutures into the passageway through the vessel clamping pressure device 800 formed by the slits. This passes the sutures through the spindle 804. A clinician may press the vessel clamping pressure device 800 against the incision site while tensioning the sutures above the device, and then rotate the spindle 804, which binds the sutures between the interior portion 810 and a corresponding surface on the central shaft 802. Binding the sutures in this manner maintains the tension in the sutures between the vessel clamping pressure device 800 and the suture site, thereby maintaining the pressure applied to the incision site by the pressure applying surface 106. To release the pressure on the incision site, a clinician may rotate the spindle 804 to realign the slits 814 in the interior portion 810 with the slits 806, 808 in the central shaft 802 and pressure applying surface 106, which releases the sutures and enables the vessel clamping pressure device 800 to be removed from the sutures.

The foregoing method descriptions and the process flow diagrams are provided merely as illustrative examples and are not intended to require or imply that the operations of various embodiments must be assembled or performed in the order presented. As will be appreciated by one of skill in the art the order of operations in the foregoing embodiments may be performed in any order. Words such as "thereafter," "then," "next," etc. are not intended to limit the order of the operations; these words are used to guide the reader through the description of the methods. Further, any reference to claim elements in the singular, for example, using the articles "a," "an," or "the" is not to be construed as limiting the element to the singular.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

What is claimed is:

1. A method of closing an incision in a vascular vessel in a patient, comprising:

closing the incision in the vascular vessel using sutures threads, and extending the suture threads from an entrance incision in the patient;

inserting an extent of the suture threads extending from the entrance incision into a vessel clamping pressure device, wherein the vessel clamping pressure device comprises:

a pressure applying surface with a surface slit, wherein the pressure applying surface is configured to contact the skin of the patient and is formed with a thickness extending in a first direction configured to extend directly away from the skin of the patient when in contact therewith, wherein the surface slit extends through the thickness of the pressure applying surface in the first direction, wherein the surface slit also extends from a lateral edge of the pressure applying surface toward a central portion of the pressure applying surface in a second direction lateral to the first direction, a central shaft with a shaft slit, wherein the central shaft extends away from the pressure applying surface in the first direction from a first side of the central shaft that connects to the pressure applying surface to a second side of the central shaft that is opposed to the first side, wherein the shaft slit extends through the central shaft from the first side to the second side and is open along a lateral side of the central shaft that extends between the first side and the second side, and a spindle located within the central shaft, the spindle including a spindle slit, wherein inserting the extent of the suture threads comprises inserting the extent of the suture threads to extend through the surface slit, shaft slit, and spindle slit;

tensioning the suture threads between the vessel clamping pressure device and the patient;

leaving the vessel clamping pressure device on the entrance incision for a clotting period; and after the clotting period, releasing tension on the suture threads and cutting the sutures threads below the vessel clamping pressure device.

2. The method of claim 1, wherein tensioning the suture threads between the vessel clamping pressure device and the patient comprises:

pulling on the suture threads extending from the vessel clamping pressure device while pressing the pressure applying surface against skin of the patient; and changing an orientation of the spindle relative to the central shaft to maintain tension on the suture threads.

3. The method of claim 2, wherein changing the orientation of the spindle relative to the central shaft comprises rotating the spindle around an axis extending in a third direction approximately 90 degrees from the first direction.

4. The method of claim 1, wherein tensioning the suture threads between the vessel clamping pressure device comprises:

rotating the spindle in the vessel clamping pressure device to pull the vessel clamping pressure device against the patient to apply pressure to the entrance incision in the patient.

5. The method of claim 1, wherein inserting the extent of the suture threads into the vessel clamping pressure device comprises positioning the vessel clamping pressure device such that the pressure applying surface is oriented toward the entrance incision.

6. The method of claim 1, wherein the clotting period is between 5 minutes and 30 minutes, and wherein releasing tension on the suture threads comprises rotating the spindle to realign the surface slit, shaft slit, and spindle slit.

7. A surgical vessel closing pressure device, comprising:

a pressure applying surface configured to contact a patient's skin or intermediate materials on the patient's skin at an incision site, wherein the pressure applying surface is formed with a thickness extending in a first direction configured to extend directly away from the skin of the patient when in contact therewith, wherein the pressure applying surface includes a first slit extending therethrough, wherein the first slit extends through the thickness of the pressure applying surface in the first direction, wherein the first slit also extends from a lateral edge of the pressure applying surface toward a central portion of the pressure applying surface in a second direction lateral to the first direction;

a central shaft coupled to the pressure applying surface, wherein the central shaft extends away from the pressure applying surface in the first direction from a first side of the central shaft that connects to the pressure applying surface to a second side of the central shaft that is opposed to the first side, wherein the central shaft includes a second slit extending therethrough, wherein the second slit extends through the central shaft from the first side to the second side and is open along a lateral side of the central shaft that extends between the first side and the second side; and a spindle adjustably located within the central shaft and rotatable about a longitudinal axis of the spindle, the spindle including a third slit extending through the spindle laterally relative to the longitudinal axis, wherein the first, second, and third slits are configured to be selectively alignable and misalignable by rotation of the spindle to respectively allow insertion of suture threads into the first, second, and third slits and bind the suture threads by adjusting an orientation of the spindle to maintain tension between the device and a vascular vessel.

8. The device of claim 7, wherein the first, second, and third slits are configured to align when the spindle is in a first rotational position to allow suture threads to be inserted therein.

9. The device of claim 8, wherein the first, second, and third slits are configured to misalign when the spindle is rotated to a second rotational position to bind the suture threads between a spindle interior portion and the central shaft.

10. The device of claim 7, wherein the pressure applying surface is wider than the central shaft.

11. The device of claim 7, wherein the pressure applying surface and the central shaft are integrally formed as a single structure.

* * * * *